(12) United States Patent
Magidson et al.

(10) Patent No.: US 6,440,339 B1
(45) Date of Patent: Aug. 27, 2002

(54) METHOD OF MAKING A CORDED EARPLUG

(75) Inventors: Mark Magidson, Culver City; Crest K Turdjiam, Los Angeles, both of CA (US)

(73) Assignee: Moldex-Metric, Inc., Culver City, CA (US)

( * ) Notice: Subject to any disclaimer, the term of this patent is extended or adjusted under 35 U.S.C. 154(b) by 0 days.

(21) Appl. No.: 09/417,578

(22) Filed: Oct. 14, 1999

(51) Int. Cl.[7] ............ B29C 39/10; B29C 44/12
(52) U.S. Cl. .............. 264/46.4; 264/157; 264/271.1
(58) Field of Search ............... 264/157, 46.4, 264/271.1

(56) References Cited

U.S. PATENT DOCUMENTS

| | | | | |
|---|---|---|---|---|
| 3,833,701 A | * | 9/1974 | Johnson et al. | 264/222 |
| 4,186,742 A | * | 2/1980 | Donald | 604/515 |
| 4,193,396 A | * | 3/1980 | Wacker | 128/152 |
| 4,219,018 A | * | 8/1980 | Draper, Jr. | 128/152 |
| 4,309,997 A | * | 1/1982 | Donald | 604/11 |
| 4,372,904 A | * | 2/1983 | Gunn | 264/279.1 |
| 4,867,149 A | * | 9/1989 | Falco | 128/864 |
| 5,483,027 A | * | 1/1996 | Krause | 181/135 |
| 5,727,566 A | * | 3/1998 | Leight | 128/857 |
| 5,799,658 A | * | 9/1998 | Falco | 128/864 |
| 6,074,060 A | * | 6/2000 | Bruce | 351/158 |
| 6,148,821 A | * | 11/2000 | Falco | 128/864 |

\* cited by examiner

*Primary Examiner*—Allan R. Kuhns
(74) *Attorney, Agent, or Firm*—Charles H Schwartz

(57) ABSTRACT

A corded earplug and a method of making a corded earplug, including providing a flexible cord material. Providing a mold member having at least one mold opening of a shape to produce at least an earplug portion inserting a short portion of the flexible cord material into the interior of the mold opening. Providing plastic material to form the earplug portion, and injecting the plastic material into the mold opening to surround the short portion of the cord material and to integrally form the earplug portion with the short portion of the cord material bonded within the earplug portion.

3 Claims, 2 Drawing Sheets

METHOD OF MAKING A CORDED EARPLUG

BACKGROUND OF THE INVENTION

The present invention relates to a corded earplug and specifically to a method for making such a corded earplug.

In the prior art, corded earplugs are generally made by initially making an earplug by any conventional technique. The earplugs are either produced with an elongated opening at one end an elongated opening is made at hole at one end of the earplug after it has been produced. An adhesive is then applied to the opening and one end of a cord is inserted into the elongated opening during the short time that the adhesive is liquid. This adhesive then bonds the cord within the opening at one end of the earplug and generally a pair of such earplugs are located at opposite ends of the cord. This produces the conventional type of corded earplug, which includes a number of additional steps after the earplugs are produced.

The difficulty with prior art corded earplugs is that it is difficult to insert the cord into the opening during the short period of time that the adhesive is liquid. In addition this method of attaching the cord to the earplug can result in a bond which is completely dependent on the adhesive and therefore may not be very strong. It would therefore be desirable to provide for a method of attaching a cord to an earplug using a method, which is simpler than the prior art and also produces strong bonding between the cord and the earplug.

SUMMARY OF THE PRESENT INVENTION

The present invention is directed to a corded earplug, and specifically to a method of making such a corded earplug, which provides for inserting the ends of the cord into openings in an injection mold. The mold is with plastic and with this occurring either before or after the mold is closed. For example the plastic can be injected and then the mold is quickly closed to have the plastic formed in the mold around the ends of the cord. Alternatively, the plastic may be injected into the mold after the cord ends are inserted and the mold closed.

Because of this technique, the molded plastic is formed around the cord itself to produce a very strong bond to the cord. In some instances when the cord material and the plastic material are similar in nature the bond can be very intimate since as the plastic sets up in the mold and bonds on a molecular basis to the cord. In other instances when the materials are different, such as when the molded earplug is a foam material, as the foam material foams it will lock tightly onto cord ends. In all instances since the molding is a hot process this tends to soften the cord again providing for an intimate bond between the cord and the earplug.

The present invention is disclosed with reference to two types of earplugs, one of a foam molded type and the other of an earplug made out of a resilient elastomeric rubber-like material similar in nature to the cord itself. The methods for making these two types of corded earplugs both incorporate the use of the ends of the cords being inserted into a mold and with the earplug then molded around the cord end. One embodiment provides for the entire earplug to be molded at the same time. The second embodiment discloses molding a portion of an earplug around the cord and with the portion of the earplug then incorporated with a flanged portion to produce a particular type of flanged earplug.

DETAILED DESCRIPTION OF THE DRAWINGS

Figure 1:
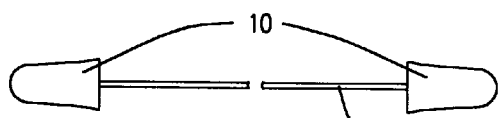
FIG. 1 illustrates a corded earplug of a first type showing a pair of earplugs at opposite ends of a cord.

As shown in FIG. 1, a first embodiment of a corded earplug includes a pair of foam earplugs 10 located at the end of a flexible elastomeric plastic cord 12. Foam earplugs may be of any type of foam earplugs currently on the market such as foam earplugs made of slow recovery foam. This type of foam can be rolled down and inserted into the ear and then the foam expands in the ear after a short passage of time. The cord 12 may be formed of a smooth plastic or may be formed of some cloth-like woven or braided material. In any event the use of the cord 12 to support the earplugs 10 is a useful feature. The earplugs can be inserted into the ear and then removed and with the cord draped around the neck to keep the earplugs located with user without having to store the earplugs in some other place.

Figure 2A:
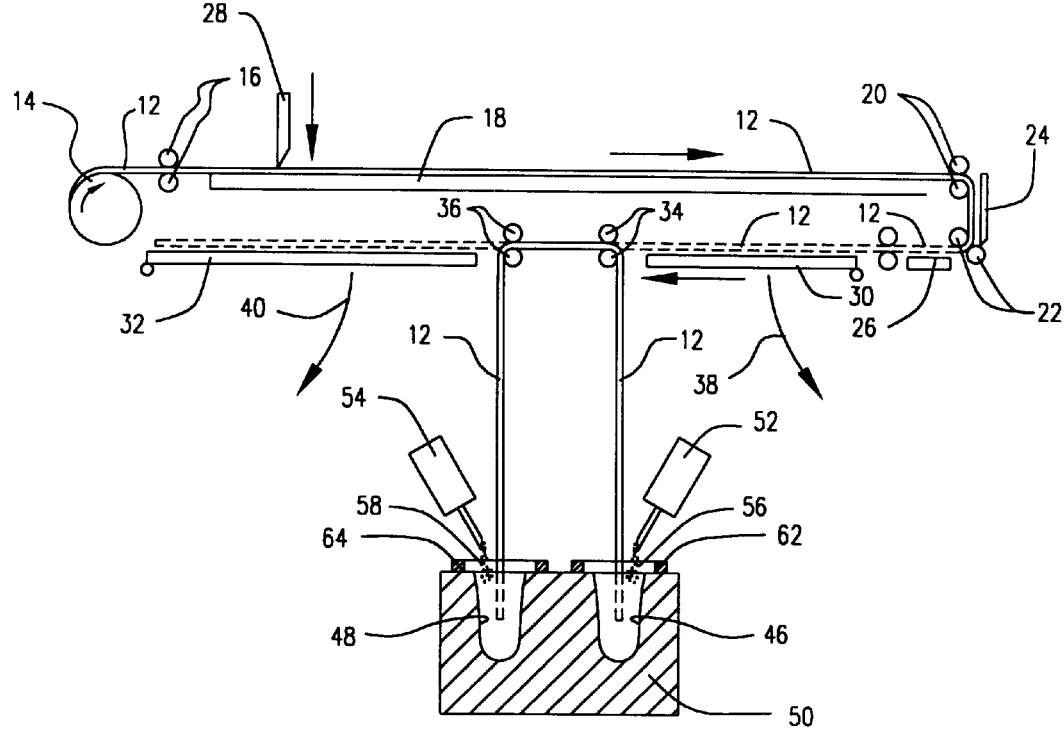
FIGS. 2A, 2B and 2C illustrates an apparatus and method for producing the corded earplug of FIG. 1.
Figure 2B:
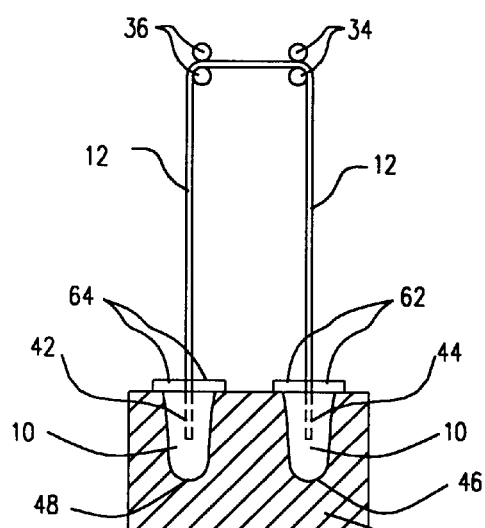
Figure 2C:
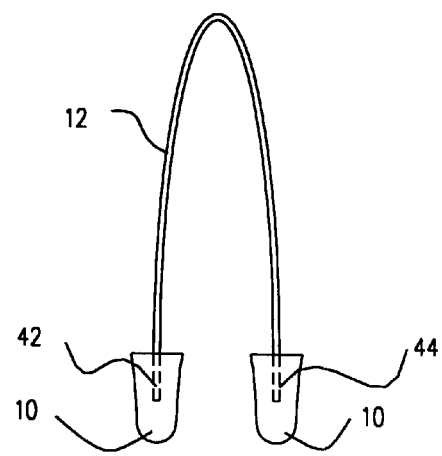

FIGS. 2A, 2B and 2C illustrates an apparatus and method for producing the corded earplugs of the type shown in FIG. 1. In particular as shown in FIG. 2A a drum 14, which contains the cord material 12 is rotated to dispense the cord material through a pair of rollers 16. The cord 12 is then support by a plate 18 having a sufficient length to play out a desired length of cord material 12. Sets of rollers 20 and 22 plus a plate 24 guide the cord material to engage a further plate 26. As the cord 12 engages the plate 26 a cutter 28 moving in the direction shown by the arrow cuts the cord against the plate 18. A particular length of cord is now produced between the position of the cutter and where the cord initially engages the plate 26.

As shown by the cord 12 in dotted position, this length may now be moved forward over plates 30 and 32. Sets of rollers 34 and 36 are located between plates 30 and 32. When the cord 12 is in the position as shown by the dotted lines, the plates 30 and 32 are pivoted downward as shown by arrows 38 and 40 to have the cords drape downward. The ends of the cords 42 and 44 hang downward to enter into earplug openings 46 and 48 in a mold body 50. As can be seen the openings 46 and 48 are the shape of the earplug 10 shown in FIG. 1.

Injectors 52 and 54 inject foam plastic material 56 and 58 into the openings 46 and 48. After desired amount of foam material is injected then sets of sliding plates 62 and 64 move over and close off the openings 46 and 48 as shown in FIG. 2B. This allows the foam material 56 and 58 to fully set up within the mold openings 46 and 48 and form earplugs molded around the ends 42 and 44 of the cord 12. After the earplugs 10 have fully set up and bonded to the ends 42 and 44 of cord 12, the sets of sliding plates 62 and 64 are moved outward and the earplugs are released from the mold 50. This produces the corded earplugs shown in FIG. 2C with the ends 42 and 44 of the cord 12 shown in dotted lines within the earplugs 10.

As indicated above, the advantages of this type of process is that the cords are molded within the earplugs, at the same time that the earplugs are made thereby eliminating a number of steps in the process of making corded earplugs. Also this type of structure provides for a better bond between the cord and earplugs.

Figure 3:
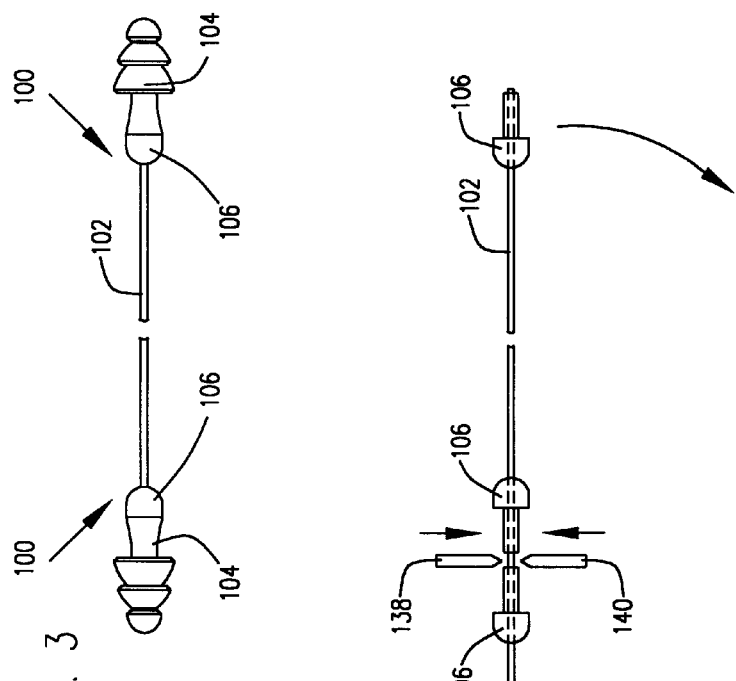
FIG. 3 illustrates of a corded flanged earplug of a second type formed of two pieces.

FIG. 3 illustrates a corded earplug of a second type including a pair of flanged earplugs 100 connected by a cord 102. The cord may be of the same type as cord 12 and, for example, may be a flexible smooth elastomeric plastic. The flanged earplugs themselves are of the type constructed of two pieces and for a more detailed disclosure of this flanged earplug, reference is made to U.S. Pat. No. 5,957,136 assigned to the same assignee as the instant application. This type of earplug has a two piece construction and includes a flexible flanged front end 104 and with a rounded back end 106 made of a harder material than the front end 104. The cord 102 is attached to the back end 106.

Figure 4:
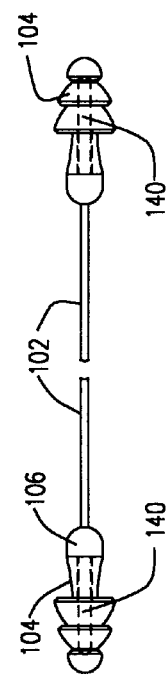
FIG. 4 illustrates an apparatus and method for producing the corded earplug of FIG. 3.
Figure 4:
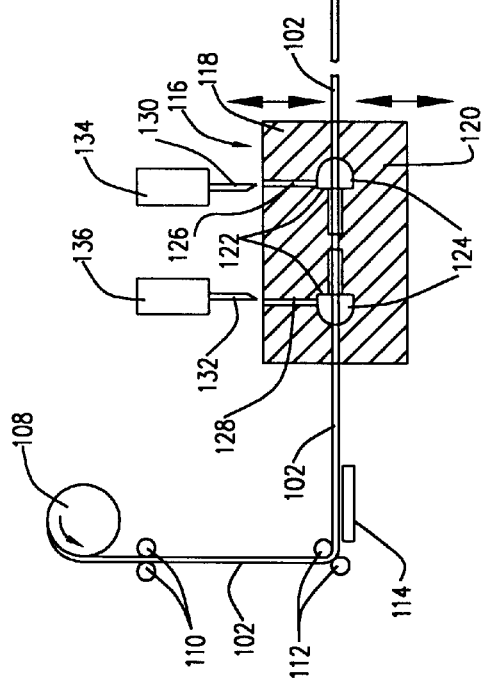

FIG. 4 illustrates a continuous process for producing the corded back end 106 of the earplug 100. In particular, a drum 108 containing a supply of cord material 102 dispenses cord material using pairs of rollers on 110 and 112 and plate member 114 to direct the cord 102 into a molding station. The molding station includes a split mold 116 including a pair of half mold members 118 and 120. Each of the mold members 118 and 120 include two recesses representing two halves of the back end 106 of earplugs 100. Mold member 118 includes mold portions 122 and mold member 120 includes mold portions 124.

When the mold members 118 and 120 are moved together they form two interior chambers representing two earplug portions 106. The cord 102 passes completely through the mold 116 to have the cord extending completely from the mold body. Plastic material is injected through ports 126 and 128 through injection nozzles 130 and 132 which are supplied by plastic supply reservoirs 134 and 136. It can be seen, therefore, that the elastomeric plastic material surrounds and contains the cord 122 during the molding process.

After the plastic material has set up, the mold members 118 and 120 are separated as shown by the arrows and the now molded earplug members 106 are moved to a cutting station as represented by cutters 138 and 140. The cutting actually occurs in the position in between the pairs of earplugs portions 106. Each time the cutting operations occurs this produces a pair of earplug portions 106 located at opposite ends of the cord 102. As a final step in the process, the earplug portions 106 are inserted into openings 140 in the flanged earplug portions 104 to form the complete corded earplug as shown in FIGS. 3 and 4.

As with the embodiment shown in FIGS. 1 and 2, the embodiment shown in FIGS. 3 and 4 produces a corded earplug where the cord is securely bonded to the ends of the earplugs. In particular, with the earplugs molded around the ends of the cords to produce for the intimate bonding of the cord within the earplug. This simplifies the process and eliminates the difficulties of the prior art of applying an adhesive and then inserting the cord into the end of an earplug during the short time that the adhesive is liquid. The method shown in the present invention provides for an extremely strong bond between the cord and the end of the earplug.

Although the invention has been described with reference to particular embodiments, it should be appreciated that various adaptations and modifications may be made and the invention is only to be limited by the appended claims.

What is claimed is:

1. A method of making a corded earplug, including the following steps providing a flexible cord material, providing a mold member having at least one mold opening of a shape to produce at least an earplug portion, inserting a short portion of the flexible cord material into the interior of the mold opening, providing plastic material to form the earplug portion, injecting the plastic material into the mold opening to surround the short portion of the cord material and to thereby integrally form the earplug portion with the short portion of the cord material bonded within the earplug portion, and the mold opening having a shape to produce a back portion of a two piece earplug and inserting the short portion of the flexible cord completely through the mold opening to have the cord extend completely through the back portion of a two piece earplug.

2. The method of claim 1 wherein the plastic material is foamable to form a foam earplug portion.

3. The method of claim 1 wherein the mold member has a pair of mold openings each having a shape to produce a back portion of a two piece earplug and with the pair of mold openings located back to back and the flexible cord is inserted completely through the pair of back to back mold openings to have interconnected short portions of the cord within the pair of mold openings and including the additional step of cutting the interconnection between the short portions of the cord to have the cord extend from the back end of each of the back portions of each of the two piece earplugs.

* * * * *